US011085855B2

(12) United States Patent
Schlaudraff et al.

(10) Patent No.: US 11,085,855 B2
(45) Date of Patent: Aug. 10, 2021

(54) LASER MICRODISSECTION METHOD AND LASER MICRODISSECTION SYSTEMS

(71) Applicant: LEICA MICROSYSTEMS CMS GMBH, Wetzlar (DE)

(72) Inventors: Falk Schlaudraff, Butzbach (DE); Andrew K. Lee, Allen, TX (US)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 353 days.

(21) Appl. No.: 16/310,825

(22) PCT Filed: Jun. 27, 2017

(86) PCT No.: PCT/EP2017/065788
§ 371 (c)(1),
(2) Date: Dec. 18, 2018

(87) PCT Pub. No.: WO2018/002011
PCT Pub. Date: Jan. 4, 2018

(65) Prior Publication Data
US 2020/0309648 A1    Oct. 1, 2020

(30) Foreign Application Priority Data

Jun. 29, 2016   (DE) .................... 10 2016 111 938.5

(51) Int. Cl.
*G01N 1/28* (2006.01)
*G01J 1/42* (2006.01)
(Continued)

(52) U.S. Cl.
CPC ............ *G01N 1/286* (2013.01); *A61B 18/20* (2013.01); *G01J 1/4257* (2013.01); *G02B 21/08* (2013.01); *G01N 2001/2886* (2013.01)

(58) Field of Classification Search
CPC ...... G01N 1/286; G01N 1/288; G01N 1/2886; G01N 1/4257; G01N 1/28;
(Continued)

(56) References Cited

U.S. PATENT DOCUMENTS 5,998,129 A * 12/1999 Schutze ................ B01L 3/0244
                                                    435/283.1
8,722,357 B2    5/2014 Baer et al.
(Continued)

FOREIGN PATENT DOCUMENTS

DE          10057292 A1    7/2002
DE          10322348 A1    12/2004
(Continued)

OTHER PUBLICATIONS

J. Rodriguez-Canales, et al., "Microdissection Technology and Challenges", National Cancer Institute, Mar. 17, 2009, pp. 1-50.
(Continued)

*Primary Examiner* — Jason L McCormack
(74) *Attorney, Agent, or Firm* — Leydig, Voit & Mayer, Ltd.

(57) ABSTRACT

A method for performing a laser microdissection for cutting a dissectate from a specimen using a laser includes the step of providing the specimen in a light path of an illumination system. The specimen is illuminated by the illumination system. A detector detects light emanating from the specimen. The light detected by the detector is analyzed. It is determined, based on the analysis of the light detected by the detector, whether a receptacle for collecting the dissectate is disposed in a predetermined collection position, at which the dissectate is to be collected in the receptacle after it is cut from the specimen. Laser cutting of the dissectate from the specimen is initiated based on it having been determined that the receptacle is in the predetermined collection position.

7 Claims, 3 Drawing Sheets

(51) Int. Cl.
*G02B 21/08* (2006.01)
*A61B 18/20* (2006.01)

(58) Field of Classification Search
CPC .... G01N 2001/2886; G01N 2035/0491; G01J 1/4257; G02B 21/08; G02B 21/36; G01V 8/00; G01V 8/10; A61B 18/20
USPC .......................................................... 600/310
See application file for complete search history.

(56) References Cited

U.S. PATENT DOCUMENTS

| | | | |
|---|---|---|---|
| 2002/0061261 A1* | 5/2002 | Pfeifer | G02B 21/26 422/400 |
| 2007/0153369 A1 | 7/2007 | Schutze et al. | |
| 2014/0152800 A1* | 6/2014 | Fomitchov | G02B 21/16 348/79 |
| 2015/0125363 A1 | 5/2015 | Schlaudraff | |
| 2015/0181094 A1* | 6/2015 | Fujii | G02B 21/008 348/79 |
| 2016/0139050 A1* | 5/2016 | Wuite | G02B 21/32 436/94 |

FOREIGN PATENT DOCUMENTS

| | | |
|---|---|---|
| DE | 102004022484 A1 | 1/2006 |
| DE | 102013209455 A1 | 11/2013 |
| WO | WO 2007115374 A1 | 10/2007 |

OTHER PUBLICATIONS

OLYMPUS CellCut Plus Microdissection, Aug. 19, 2010, pp. 1-4.
OLYMPUS Laser Microdissection System—CellCut—for IX2 Microscopes, May 11, 2006, pp. 1-26.
ZEISS Die PALM Familie—Eine neue Dimension der Probeneinheit, Mar. 28, 2012.
ZEISS PALM RoboSoftware Software Manual MicroLaser Systems Version 3.1-0106 (EN), Sep. 5, 2008, pp. 1-154.
Leica LMD6500 Leica LMD7000 Laser Microdissection Systems—Dissection perfection Produktbroschüre Jun. 8, 2015.
Leica LMD6 Leica LMD7 Laser Microdissection Systems—Dissection perfection Produktbroschüre, Mar. 24, 2016, pp. 1-16.
Elvers, D., et al., „Laser microdissection of biological tissues: process optimization, Applied Physics A: Materials Science & Processing, vol. 80, No. 1, Dec. 2005, pp. 55-59.
ArcturusXT™ Laser Capture Microdissection (LCM) System Quick Reference Guide, Jun. 29, 2010, pp. 1-2.
ArcturusXT™ Laser Capture Microdissection System User Guide (PN 0112-0153C), Nov. 11, 2010.
Konrad Kölble, "The LEICA microdissection system: Design and applications", J Mol Med, vol. 78, Dec. 2000, pp. B24-B25.

\* cited by examiner

LASER MICRODISSECTION METHOD AND LASER MICRODISSECTION SYSTEMS

CROSS-REFERENCE TO PRIOR APPLICATIONS

This application is a U.S. National Stage Application under 35 U.S.C. § 371 of International Application No. PCT/EP2017/065788 filed on Jun. 27, 2017, and claims benefit to German Patent Application No. DE 10 2016 111 938.5 filed on Jun. 29, 2016. The International Application was published in German on Jan. 4, 2018, as WO 2018/002011 A1 under PCT Article 21(2).

FIELD

The present invention relates to a method for performing a laser microdissection for cutting a dissectate from a specimen using a laser, and a laser microdissection system for a performing laser microdissection.

BACKGROUND

In the fields of biology and medicine, laser microdissection refers to a method by which a particular portion of a specimen (e.g., individual cells, cell clusters, or a tissue section)—a so-called dissectate—is cut from the specimen using a focused laser beam. For this purpose, the specimen can be provided on a planar support—for example, a glass specimen support or a polymer film. In typical arrangements, the dissectate falls, after it is cut from the specimen, in a downward direction into a receptacle under gravity. After the cut, the dissectate is available for further biological or medical (for example, histological) examinations.

SUMMARY

In an embodiment, the present invention provides a method for performing a laser microdissection for cutting a dissectate from a specimen using a laser. The specimen is provided in a light path of an illumination system. The specimen is illuminated by the illumination system. A detector detects light emanating from the specimen. The light detected by the detector is analyzed. It is determined, based on the analysis of the light detected by the detector, whether a receptacle for collecting the dissectate is disposed in a predetermined collection position, at which the dissectate is to be collected in the receptacle after it is cut from the specimen. Laser cutting of the dissectate from the specimen is initiated based on it having been determined that the receptacle is in the predetermined collection position.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
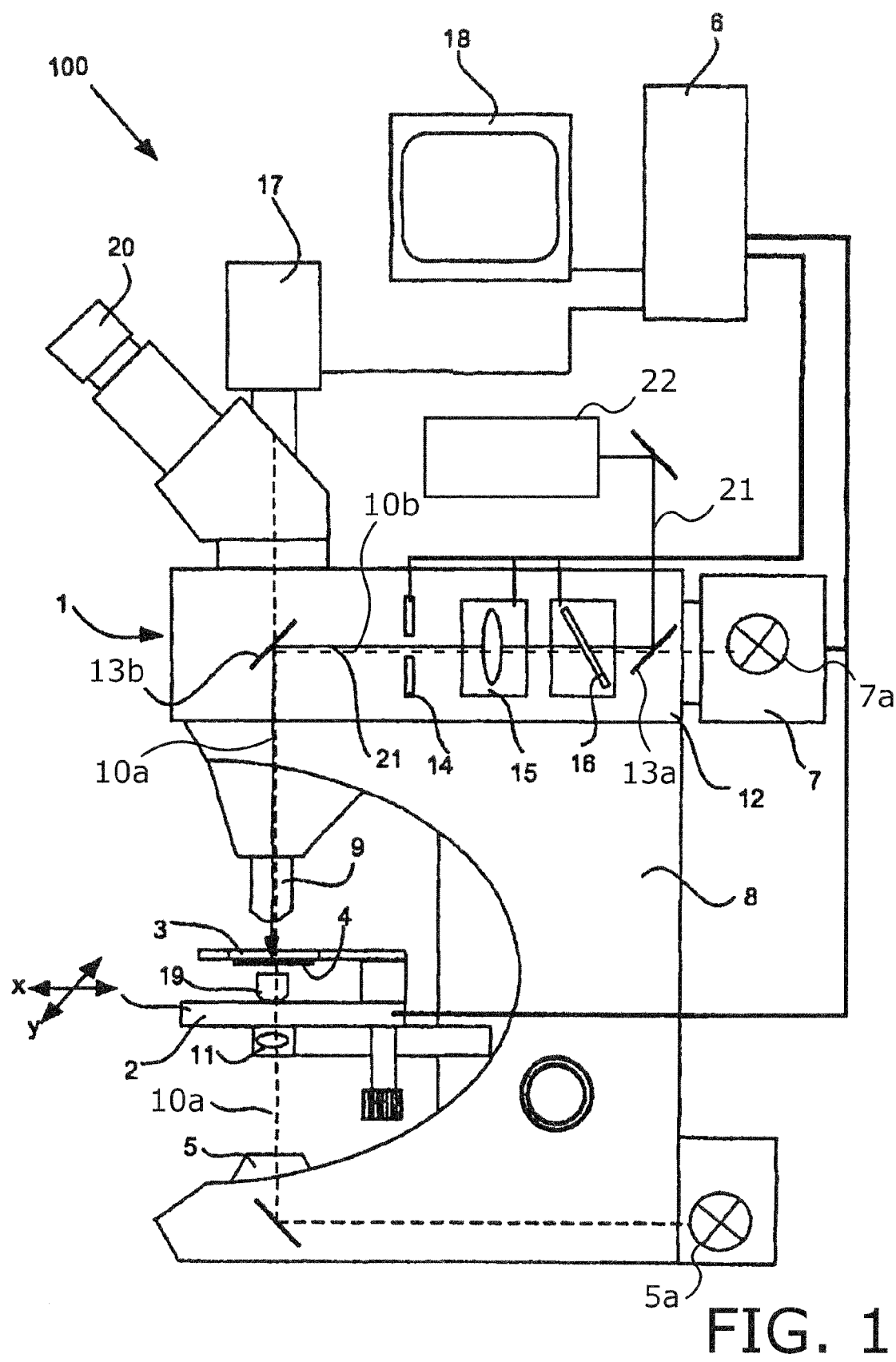
FIG. 1 schematically shows a preferred embodiment of a laser microdissection system according to the invention that is designed to implement a preferred embodiment of a method according to the invention.

It is recognized in the invention that, if a receptacle is not provided in the laser microdissection system at the position where the dissectate falls, e.g., because a user has forgotten to provide the vessel before the start of the cutting process, the dissectate will probably be lost. Embodiments of the present invention improve laser microdissection systems and laser microdissection methods so that this disadvantage can be prevented.

Embodiments of the invention provide a method for performing a laser microdissection for cutting a dissectate from a specimen using a laser, and a laser microdissection system for performing a laser microdissection.

The method according to an embodiment of the invention comprises the steps of providing the specimen in a light path of an illumination system; illuminating the specimen by means of the illumination system; by means of a detector, detecting light emanating from the sample; analyzing the light detected by the detector; on the basis of the analysis, determining whether a receptacle for collecting the dissectate is provided at a predetermined collection position, in which the dissectate is collected in the receptacle after it is cut from the specimen; and initiating laser cutting of the dissectate from the specimen only when it is determined that the receptacle is in the predetermined collection position. Light emanating from the specimen may, in particular, be light that is transmitted through the specimen, and/or light that is reflected by the specimen, and/or light that is re-emitted by the specimen.

An embodiment of the invention consequently makes it possible to determine reliably, easily, and automatically whether a receptacle is provided in the collection position of the laser microdissection system. As long as no receptacle is detected, the laser cutting process is not started. Accordingly, the laser cutting process can be prevented from being inadvertently started without providing a receptacle in the collection position, and, consequently, the dissectate cut from the specimen from being lost. According to an embodiment of the invention, the corresponding laser microdissection system automatically checks whether a receptacle is provided in the collection position, without additional effort by the user.

The determination and analysis are, in particular, carried out by a control unit of the laser microdissection system, which, usefully, also controls the laser. Determination can thus easily be integrated into the regular control of the microdissection process. By means of this control unit, a desired part of the specimen to be cut as the dissectate can be selected, in particular, by a user. In particular, the control unit can also be designed to determine parameters by which the laser is controlled in order to cut the dissectate from the specimen.

The illumination system is, expediently, a part of a microscope—in particular, a transmitted-light microscope and/or an incident-light microscope. By means of such a microscope, an enlarged image of the specimen, or a portion of interest from the specimen, can be determined. In particular, the user selects the desired portion of the specimen to be cut as the dissectate by using such an enlarged image.

In particular, the predetermined collection position in which the receptacle is provided is arranged in the light path of the illumination system. When the receptacle is arranged in this predetermined collection position, the light detected by the detector is therefore influenced in a particular way by the receptacle, or the light acts upon the receptacle. This change in light properties is characteristic, for example, of the specific type of receptacle, illumination, and/or contrast method. Consequently, the light detected by the detector can be used for determining whether the receptacle is provided in the collection position. In the course of such a determination, the detected light is therefore usefully analyzed with regard to this change in the light characteristics caused by the receptacle.

After the receptacle is provided in the light path of the illumination system, the detected light is, for example, in particular, less bright or brighter, and/or has a lower intensity, and/or is no longer focused on the detector. A change in the frequency spectrum may also be observed. Thus, by specifically searching for any of these features or differences in the detected light, it can be effectively determined whether the receptacle has been provided in the collection position.

The specimen is preferably illuminated by the illumination system in the course of a transmitted-light illumination and/or an incident-light illumination. The specimen is, in particular, illuminated from below (with respect to the detector) by means of transmitted-light illumination. Light transmitted through the specimen is, advantageously, detected by the detector.

In the course of the incident-light illumination, the specimen is, expediently, illuminated from the top or above. For example, the specimen may reflect a portion of the illumination light and/or may be excited by the illumination light so that the specimen re-emits light. This reflected or re-emitted light is preferably detected by the detector.

In an advantageous embodiment, the analysis comprises a comparison of the light detected by the detector in a first mode, in which it is known that no receptacle is provided in the predetermined collection position, with light that is detected by the detector in a second mode, in which it is assumed or presupposed that a receptacle is provided in the predetermined collection position.

Preferably, the laser microdissection process of the invention is carried out as follows: In a first mode, the specimen is, initially, provided in the light path of the illumination system. The specimen is illuminated by means of the illumination system. Light transmitted through the specimen (in the case of transmitted-light illumination) and/or light emitted by the specimen (in the case of incident-light illumination) is detected by means of the detector. Usefully, a receptacle is not yet provided, in order to effectively illuminate the specimen. The user, expediently, selects a desired portion of the specimen to be cut as a dissectate.

Then, the receptacle is arranged manually or automatically in the predetermined collection position in the light path of the illumination system.

In a second mode, light is detected by the detector. Whether the receptacle has actually been provided in the collection position is then determined by comparing the light detected in the second mode with the light detected in the first mode.

As explained above, by providing the receptacle in the light path of the illumination system, the detected light is influenced in a specific way so that changes in specific features can be determined, e.g., a change in brightness, frequency, etc. Specific features can be determined in, for example, the course of a calibration process or learning process. This calibration process can, for example, be performed in the course of a manufacturing process of the corresponding laser microdissection system or of the particular receptacles. In the course of the calibration process, the receptacle can, in particular, be examined, and a particular feature of the detected light can be precisely determined.

In a preferred embodiment, the determination as to whether the receptacle is provided in the predetermined collection position is based upon a detection of a difference in the brightness of the light detected by the detector, which is caused because the receptacle is provided in the light path of the illumination system. Preferably, when this difference in brightness is detected, it is determined that the receptacle is provided in the predetermined collection position. Brightness is a preferred example of a particular feature that changes by providing the receptacle in the light path of the illumination system.

In the case of transmitted-light illumination, the brightness of the detected light is reduced, in particular, by a specific value when the receptacle is provided in the light path of the transmitted-light illumination system, since the receptacle, in particular, does not consist of a completely transparent material, such as a plastic material. Consequently, the light emanating from the specimen is reduced.

In the case of incident-light illumination, the brightness of the detected light is increased, in particular, when the receptacle is provided in the light path of the incident-light illumination system, since the receptacle, expediently, reflects light and/or re-emits light, e.g., due to autofluorescence. A portion of the light from the illumination system may, for example, be transmitted through the specimen and may contact the receptacle. A portion of this light can be reflected by the receptacle in the direction of the specimen, can be transmitted through the specimen, and can be detected by the detector. This light also emanates from the specimen, whereby all of the light emanating from the specimen is, consequently, increased.

It is possible for the control unit to automatically analyze the detected light for differences in brightness, in order to set an illumination time for the corresponding detector—for example, during a cutting process.

Another embodiment of the invention provides a laser microdissection system for performing a laser microdissection with a laser that is designed to cut a dissectate from a specimen; an illumination system that is designed to emit light along a light path; a detector that is designed to detect light, emanating from the specimen, which is provided in the light path of the illumination system; and a control unit, which is designed to perform an analysis of the light detected by the detector, is designed to determine, based upon the analysis, whether a receptacle is provided for collecting the dissectate in a predetermined collection position, in which the dissectate is collected in the receptacle after it is cut from the specimen, and is designed to initiate laser cutting of the dissectate from the specimen only once it is determined that the receptacle is located in the predetermined collection position.

The laser microdissection system according to an embodiment of the invention is, in particular, designed to carry out the method according to one of the embodiments of the invention.

Analogously to the above description of the method according to different embodiments of the invention, this laser microdissection system according to different embodiments of the invention makes it possible to easily and automatically determine whether a receptacle is provided in the predetermined collection position. The control unit is, in particular, further designed to control the laser and the cutting process. The determination can thus be easily incorporated into the regular control of the microdissection process. The illumination system is preferably a transmitted-light illumination system and/or an incident-light illumination system.

According to a preferred embodiment, the control unit is further designed, in the course of the analysis, to compare light that is detected by the detector in a first mode, in which it is known that no receptacle is provided in the predetermined collection position, with light that is detected by the detector in a second mode, in which it is presupposed that a receptacle is provided in the predetermined collection position.

According to an advantageous embodiment, the control unit is further designed to determine whether the receptacle is provided in the predetermined collection position, based upon a detection of a reduction in the brightness of the light detected by the detector, which is caused because the receptacle is provided in the light path of the illumination system.

It should be noted that the features mentioned above and the features to be described further below are useful, not only in the respective combination given, but also in additional combinations or alone, without departing from the scope of protection of the present invention.

FIG. 1 schematically shows a preferred embodiment of a laser microdissection system 100 according to the invention designed to implement a preferred embodiment of a method according to the invention.

The laser microdissection system 100 is designed to perform a laser microdissection for cutting a dissectate using a laser 22 from a specimen 4 in the course of a cutting process. The specimen 4 is placed on a lower surface of specimen holder 3, for example. The laser microdissection system 100 comprises an x-y table 2 which can be moved by a motor. The specimen holder 3 and, consequently, the specimen 4 can be arranged on this x-y table 2.

The laser microdissection system 100 further comprises an illumination system 5 in the form of a transmitted-light illumination system and an illumination system 7 in the form of an incident-light illumination system. The illumination systems 5 and 7 are designed to emit light from a transmitted-light source 5a or an incident-light source 7a along a light path 10a or 10b. Thus, when the specimen holder 3 containing the specimen 4 is arranged on the x-y table 2, the specimen 4 is consequently provided in the light paths 10a and 10b of the illumination systems 5 and 7.

The specimen 4 can the illuminated by means of the transmitted-light illumination system 5 and/or by means of the incident-light illumination system 7. Light emanating from the specimen 4 is detected by means of a detector 17. In the case of transmitted-light illumination, light transmitted through the specimen 4 is detected, in particular, by means of the detector 17. In case of incident-light illumination, light reflected and/or re-emitted by the specimen 4 is detected by means of the detector 17. The illumination systems 5 and 7 can be a part of a microscope 1, which can be constructed, in particular, as a transmitted-light and/or incident-light microscope. By means of this microscope 1, an enlarged image of the specimen 4 or a part of the specimen 4 can be generated, detected by the detector 17, and output to the user on a monitor 18.

The transmitted-light illumination system 5 is, for example, arranged on a microscope stand 8 under the x-y table 2, and thus arranged below the specimen 4. The incident-light illumination system 7 may be arranged above the x-y table 2, and thus above the specimen 4. The microscope 1 comprises at least one objective 9, which is arranged above the x-y table 2, and consequently above the specimen 4. The objective 9 defines an optical axis that is aligned with the optical axis of the transmitted-light illumination system 5 and of the incident-light illumination system 7.

Light emitted by the transmitted-light illumination system 5 is directed from below a condenser 11 toward the specimen holder 3, which is arranged on the x-y table 2, with the specimen 4. The light penetrating the specimen 4 passes through the objective 9 of the microscope 1. Within the microscope, the light is directed to an eyepiece 20 via lenses and mirrors and/or prisms.

Light emitted from the light source 7a of the incident-light illumination system 7 is guided into an optical system 12 by means of a first beam splitter 13a, e.g., a dichromatic splitter. By means of a second beam splitter 13b, e.g., also a dichromatic splitter, the light is coupled from the illumination system 7 into the light path of the microscope 1, in order to illuminate specimen 4 from above.

The detector 17 is connected to the microscope 1 and a control unit 6. By means of this control unit 6, the enlarged image of the specimen or part of the specimen is displayed on the monitor 18.

Via this monitor 18, which, for example, can be provided as a touchscreen, the user can select a desired portion of the specimen 4 that is to be cut as a dissectate in the course of the cutting process. The control unit 6 can, accordingly, control the laser 22 so as to cut this desired part of the specimen.

In order to receive a dissectate after it has been cut from the specimen 4, a receptacle 19 is provided in a predetermined collection position on the x-y table 2 below the specimen holder 3, and thus below the specimen 4. When the dissectate of the specimen is removed and falls in a downward direction under gravity, it is collected in the receptacle 19 in the predetermined collection position.

If the cutting process is performed in the predetermined collection position without the receptacle 19, the dissectate is very likely to be lost. Therefore, the laser microdissection system 100—in particular, the control unit 6—is designed to implement a preferred embodiment of a method according to the invention—for example, by running corresponding software. As a result, the cutting process is initiated only when the receptacle 19 is detected as being provided in the predetermined collection position, as explained below with reference to FIG. 2 and FIG. 3.

When the cutting process is initiated, a laser beam 21 is emitted from the laser 22, which, for example, may be a UV laser 22. By means of the first beam splitter 13a, the laser beam 21 is guided into the optical system 12, which comprises optical elements 14, 15, and 16.

An aperture unit 14 may, for example, comprise an iris diaphragm, or a selection from a number of different apertures. A focusing unit 15 can be used to compensate for different focal point positions in a different spectral range. The focusing unit 15 may also be used to select a particular focal point position or a continuous variation of the focal point position of the laser focal point during the cutting operation. The angular position of a damper unit 16 may be changed, and the damping based upon the principle of interference. The laser beam 21 is coupled into the light path 10a of the microscope 1 via the beam splitter 13b.

The position and/or the size of the aperture unit 14, the focusing unit 15, and the damper unit 16 can be changed by control signals from the control unit 6. Consequently, the control unit 6 can influence the laser beam 21, in order to accurately cut the dissectate from the specimen 4. The specimen 4 is, in particular, cut with the aid of individual laser pulses. For this purpose, the control unit 6 can synchronize the laser pulses to the changes in the optical elements 14, 15, and 16 and the movements of the x-y table 2. The last laser pulse of the cutting process may, for example, be a pulse with a relatively wide aperture of the laser beam 21, in order to cut the last part of the cutting line and separate the dissectate from the specimen 4, which then falls downwards in the direction of the receptacle 19. After the dissectate is cut from the specimen 4, it is collected in the receptacle 19 in the predetermined collection position.

Figure 2:
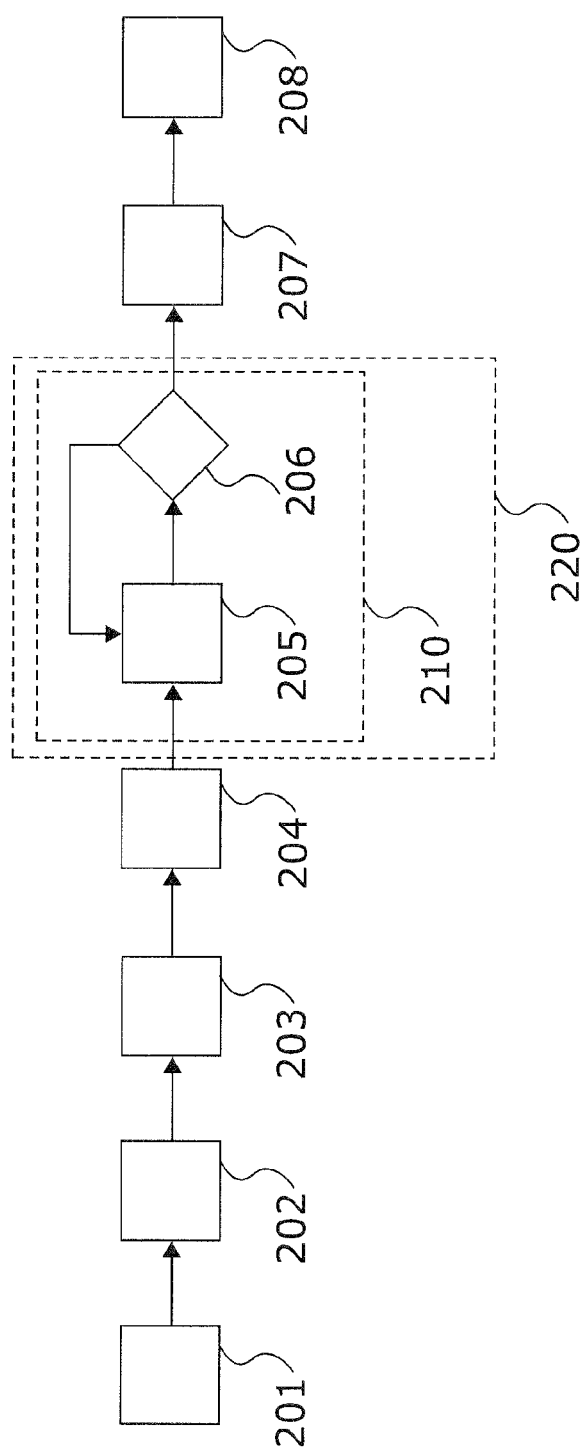
FIG. 2 schematically shows a preferred embodiment of a method according to the invention as a block diagram.

FIG. 2 schematically shows a preferred embodiment of a method according to the invention as a block diagram.

In step 201, the specimen 4 is provided in the light path 10*a* of the illumination system 5 or in the light path 10*b* of the incident-light illumination system 7. For this purpose, the specimen holder 3 is arranged on the x-y table 2.

In step 202, the illumination system 5 is activated. The specimen 4 is, consequently, illuminated by means of the illumination system 5, and light transmitted through the specimen 4 is detected by means of the detector 17. A correspondingly enlarged image of the specimen 4 is output to the user on the monitor 18.

Alternatively or additionally, the illumination system 7 can be activated. The specimen 4 reflects part of the light from the illumination 7. Moreover, the specimen 4 can be excited by part of the light and can re-emit light itself. The reflected and re-emitted light is detected by means of the detector 17.

In step 203, the user selects the desired part of the specimen 4 to be cut as the dissectate in the course of the cutting process.

Light detected by means of the detector 17 during these steps 202 and 203 is detected in a first mode, in which it is known that no receptacle is provided in the predetermined collection position. Preferably, a first brightness value of the detected light is detected in this first mode.

After this desired part has been selected, the receptacle 19 is arranged, automatically or manually, in the predetermined collection position in step 204. For example, by pressing a particular button on the touch screen 18, the collection tray 19, for example, may be automatically provided and positioned by a corresponding positioning system.

An analysis 210 is carried out by the control unit 6. In the course of this analysis 210, the control unit 6 analyzes the light detected by the detector 17. Moreover, the control unit 6 carries out a determination 220 as to whether the receptacle 19 is provided in the predetermined collection position. This determination 220 is carried out on the basis of this analysis 210.

In the course of the analysis 210, the detected light is analyzed for specific changes—preferably, for a certain or specific difference in the brightness, which is caused by the receptacle 19 being provided in the light path of the illumination system 5 or 7.

For this purpose, the light is detected by means of the detector 17 in a second mode in step 205, in which it is assumed that the receptacle 19 is provided in the predetermined collection position. Preferably, a second brightness value of the detected light is detected in this second mode.

In step 206, the control unit 6 compares the light detected in the first mode with this light detected in the second mode. In particular, the first brightness value is compared with the second brightness value. In the course of this comparison, it is specifically evaluated whether the brightness is reduced or increased by a corresponding specific threshold value.

In the case of transmitted-light illumination, the brightness of the detection light is reduced by a corresponding threshold value when the receptacle 19 is provided in the predetermined collection position in the light path 10*a* of the illumination system 5.

The brightness is, usefully, increased by a corresponding threshold when the receptacle 19 is provided in the light path 10*b* of the incident-light illumination system 7 in the predetermined collection position.

When the specific difference in brightness is detected in step 206, it is therefore concluded that a receptacle 19 is provided in the predetermined collection position, and the control unit 6 initiates the laser cutting process in step 207. In step 208, the control unit 6 controls the cutting process and cuts the dissectate from the specimen 4.

Some elements of the laser microdissection system according to FIG. 1 are schematically shown in FIG. 3. In this particular example from FIG. 3, the specimen 4 is illuminated by means of the transmitted-light illumination system 5.

Figure 3B:
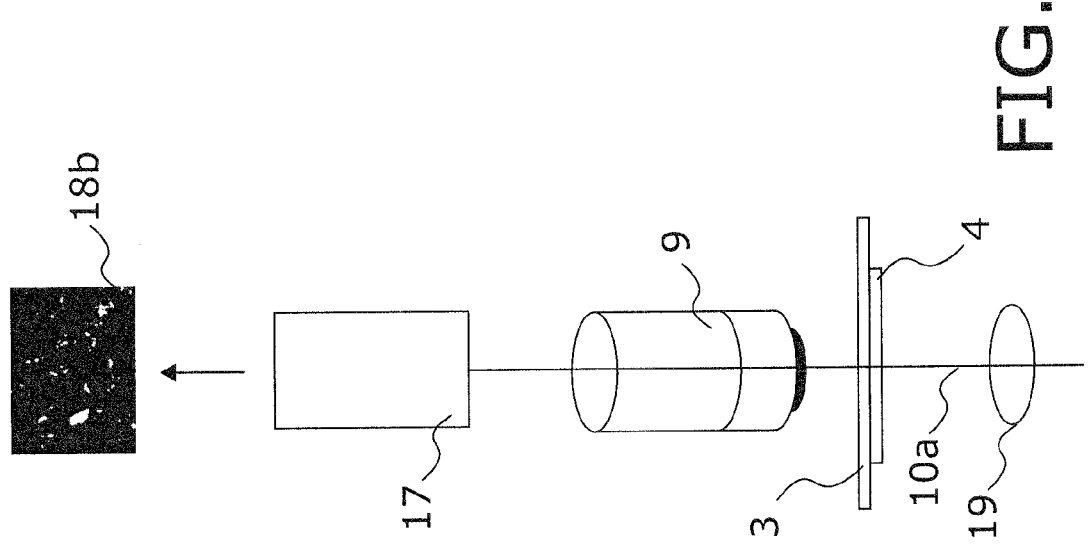
FIGS. 3a and 3b schematically show elements of a preferred embodiment of a laser microdissection system according to the invention designed to implement a preferred embodiment of a method according to the invention.
Figure 3A:
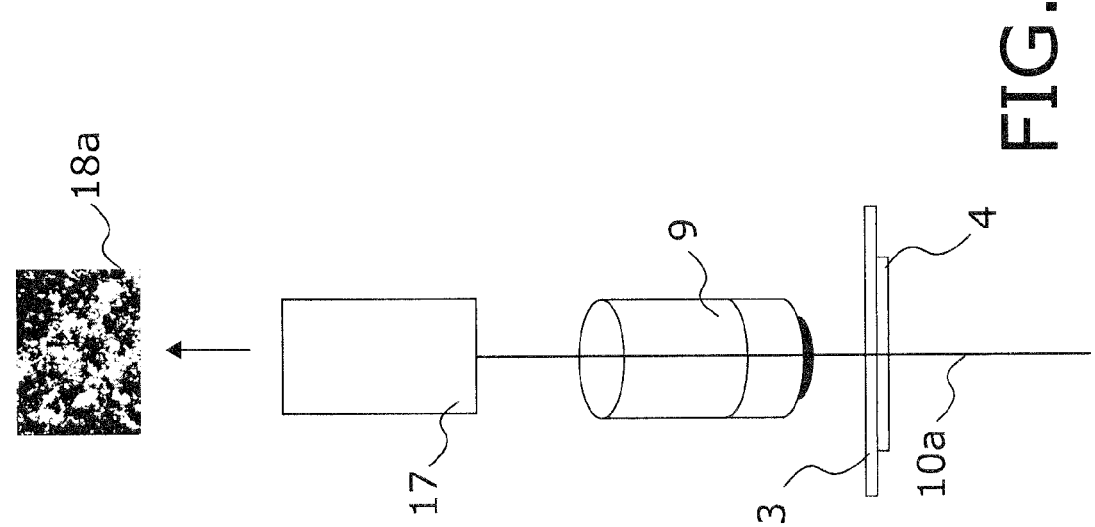

FIG. 3*a* characterizes the light detected in the first mode, in which it is known that no receptacle 19 is provided in the predetermined collection position. FIG. 3*b* characterizes the light detected in the second mode, in which the receptacle 19 is provided in the predetermined collection position in the optical path 10*a* of the transmitted-light illumination system 5.

FIG. 3*a* schematically shows an image 18*a* that can be recorded by the detector 17 in the first mode. The image 18*a* can be shown on the monitor 18 to the user.

FIG. 3*b* schematically shows a corresponding image 18*b* which can be recorded by the detector 17 in the second mode, when light transmitted through the mounted receptacle 19 and through the specimen 4 is detected. As can be seen, the brightness of the image 18*b* is less in comparison to the image 18*a*, due to the mounted receptacle 19.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMBERS

100 Laser microdissection system
1 Microscope, transmitted-light microscope
2 x-y table
3 Specimen holder
4 Specimen
5 Illumination system, transmitted-light illumination system
5a Light source
6 Control unit
7 Illumination system, incident-light illumination system
7a Light source
8 Microscope stand
9 Objective
10a Light path
10b Light path
11 Condenser
12 Optical system
13a Beam splitter
13b Beam splitter
13c Beam splitter
14 Aperture unit
15 Focusing unit
16 Damper unit
17 Detector
18 Monitor, touch screen
18a Image recorded by the detector in the first mode
18b Image recorded by the detector in the second mode
19 Receptacle
20 Eyepiece
21 Laser beam
22 Laser
201 through 208 Method steps
210 Analysis
220 Determination

The invention claimed is:

1. A method for performing a laser microdissection for cutting a dissectate from a specimen using a laser, the method comprising:
providing the specimen in a light path of an illumination system;
illuminating, by the illumination system, the specimen;
detecting, by a detector, light emanating from the specimen;
analyzing the light detected by the detector;
determining, based on the analysis of the light detected by the detector, whether a receptacle for collecting the dissectate is disposed in a predetermined collection position, at which the dissectate is to be collected in the receptacle after it is cut from the specimen; and
initiating laser cutting of the dissectate from the specimen based on it having been determined that the receptacle is in the predetermined collection position,
wherein the analysis of the light detected by the detector comprises a comparison of light that is detected by the detector in a first mode, in which it is known that no receptacle is provided in the predetermined collection position, with light that is detected by the detector in a second mode, in which it is assumed that a receptacle is provided in the predetermined collection position.

2. The method according to claim 1, wherein the determination as to whether the receptacle is provided in the predetermined collection position is based upon a detection of a difference in brightness of the light detected by the detector, which is caused by the receptacle being disposed in the light path of the illumination system.

3. The method according to claim 1, wherein the specimen is illuminated by the illumination system in the course of a transmitted-light illumination and/or an incident-light illumination.

4. A laser microdissection system for performing a laser microdissection, comprising:
a laser configured to cut a dissectate from a specimen;
an illumination system configured to emit light along a light path;
a detector disposed in the light path of the of the illumination system and configured to detect light emanating from the specimen; and
a controller configured to:
perform an analysis of the light detected by the detector;
determine, based on the analysis of the light detected by the detector, whether a receptacle for collecting the dissectate is provided in a predetermined collection position, at which the dissectate is collected in the receptacle after it is cut from the specimen; and
initiate laser cutting of the dissectate from the specimen based on it having been determined that the receptacle is in the predetermined collection position,
wherein the controller is configured to perform the analysis of the light detected by the detector by comparing light that is detected by the detector in a first mode, in which it is known that no receptacle is provided in the predetermined collection position, with light that is detected by the detector in a second mode, in which it is assumed that a receptacle is provided in the predetermined collection position.

5. The laser microdissection system according to claim 4, wherein the controller is configured to determine whether the receptacle is provided in the predetermined collection position based upon a detection of a reduction in brightness of the light detected by the detector, which is caused by the receptacle being disposed in the light path of the illumination system.

6. The laser microdissection system according to claim 4, wherein the illumination system has a transmitted-light illumination system or an incident-light illumination system.

7. A method for performing a laser microdissection for cutting a dissectate from a specimen using a laser, the method comprising:
providing the specimen in a light path of an illumination system;
illuminating, by the illumination system, the specimen;
detecting, by a detector, light emanating from the specimen;
analyzing the light detected by the detector;
determining, based on the analysis of the light detected by the detector, whether a receptacle for collecting the dissectate is disposed in a predetermined collection position, at which the dissectate is to be collected in the receptacle after it is cut from the specimen; and
initiating laser cutting of the dissectate from the specimen based on it having been determined that the receptacle is in the predetermined collection position, wherein the determination as to whether the receptacle is provided in the predetermined collection position is based upon a detection of a difference in brightness of the light detected by the detector, which is caused by the receptacle being disposed in the light path of the illumination system.

* * * * *